United States Patent
Kim et al.

(10) Patent No.: US 9,345,847 B2
(45) Date of Patent: May 24, 2016

(54) WASHING WATER SPRAYING VESSEL FOR NASAL CAVITY CLEANER

(71) Applicant: YONWOO CO., LTD., Incheon (KR)

(72) Inventors: Sung-Hwan Kim, Incheon (KR); You-seob Kim, Incheon (KR)

( * ) Notice: Subject to any disclaimer, the term of this patent is extended or adjusted under 35 U.S.C. 154(b) by 0 days.

(21) Appl. No.: 14/395,741

(22) PCT Filed: Apr. 19, 2013

(86) PCT No.: PCT/KR2013/003329
§ 371 (c)(1),
(2) Date: Oct. 20, 2014

(87) PCT Pub. No.: WO2013/157880
PCT Pub. Date: Oct. 24, 2013

(65) Prior Publication Data
US 2015/0088069 A1      Mar. 26, 2015

(30) Foreign Application Priority Data

Apr. 20, 2012   (KR) .................. 10-2012-0041652
Feb. 1, 2013    (KR) .................. 10-2012-0011625

(51) Int. Cl.
*B67B 1/00*       (2006.01)
*A61M 11/08*      (2006.01)
(Continued)

(52) U.S. Cl.
CPC ............. *A61M 11/08* (2013.01); *A61M 11/007* (2014.02); *A61M 15/08* (2013.01); *B05B 11/3015* (2013.01); *B05B 11/3023* (2013.01);
(Continued)

(58) Field of Classification Search
CPC . A61M 11/006; A61M 11/008; A61M 15/08; A61M 2210/0618; B05B 11/3009

USPC ............... 222/153.04, 153.09–153.1, 383.1, 222/383.3, 321.6–321.9, 153.13–153.14; 128/200.11–200.24, 200.26, 203.12, 128/203.15, 203.22, 207.13, 207.18; 604/27, 36–37, 48, 73, 181
See application file for complete search history.

(56) References Cited

U.S. PATENT DOCUMENTS 3,272,391 A * 9/1966 Meshberg ............ B65D 83/206
                                                            222/162
4,071,173 A * 1/1978 Horan ................. B65F 83/205
                                                            222/153.13

(Continued)

FOREIGN PATENT DOCUMENTS

KR   2005-0004845 A   1/2005
KR   2010-0006433 U   6/2010
KR   2011-0006840 U   7/2011

OTHER PUBLICATIONS

International Search Report issued in PCT/KR2013/003329 dated Aug. 19, 2013.

*Primary Examiner* — Paul R Durand
*Assistant Examiner* — Andrew P Bainbridge
(74) *Attorney, Agent, or Firm* — Marshall, Gerstein & Borun LLP (57) ABSTRACT

The present invention relates to a washing water spraying vessel for a nasal cavity cleaner. A pumping operation of a pumping member is performed only when a pair of buttons formed on both sides of an outer cap are simultaneously pressed, which allows enabling fundamentally blocking the pumping operation through external pressure unintended by a user, thereby not only preventing washing water from being unnecessarily consumed but also preventing an inner part of the overcap from being contaminated.

11 Claims, 10 Drawing Sheets

(51) Int. Cl.
*A61M 15/08* (2006.01)
*B05B 11/00* (2006.01)
*A61M 11/00* (2006.01)

(52) U.S. Cl.
CPC ......... *B05B11/3056* (2013.01); *B05B 11/3059* (2013.01); *A61M 11/006* (2014.02); *A61M 11/008* (2014.02); *A61M 2205/276* (2013.01); *A61M 2210/0618* (2013.01); *B05B 11/3009* (2013.01); *B67B 1/00* (2013.01)

(56) References Cited

U.S. PATENT DOCUMENTS

| | | | | |
|---|---|---|---|---|
| 4,991,746 A * | 2/1991 | Schultz | ................ | A47K 5/1205 222/153.13 |
| 5,337,926 A * | 8/1994 | Drobish | ................ | B05B 1/1645 222/309 |
| 5,516,006 A * | 5/1996 | Meshberg | ............. | A61M 15/08 222/162 |
| 5,615,806 A * | 4/1997 | Grothoff | ............. | B05B 11/3023 222/153.13 |
| 5,971,226 A * | 10/1999 | Goncalves | ........... | B65D 47/248 222/321.6 |
| 6,164,498 A * | 12/2000 | Faughey | ................ | G01F 11/262 222/153.13 |
| 6,419,124 B1 * | 7/2002 | Hennemann | ........ | B05B 11/0037 222/162 |
| 7,044,341 B2 * | 5/2006 | Sanchez | ............. | B05B 11/0027 222/321.6 |
| 8,096,450 B2 * | 1/2012 | Herry | .................. | B05B 11/3014 222/321.1 |
| 8,752,543 B2 * | 6/2014 | Davies | ................ | A61M 15/009 128/200.14 |
| 8,820,318 B2 * | 9/2014 | Crosby | ............... | A61M 15/009 128/200.14 |
| 8,863,988 B2 * | 10/2014 | Kang | .................... | B65D 55/02 222/153.13 |
| 2004/0004138 A1 * | 1/2004 | Hettrich | ............ | A61M 15/0065 239/569 |
| 2004/0245291 A1 * | 12/2004 | Simon | .................. | B65D 83/386 222/321.7 |
| 2005/0258191 A1 * | 11/2005 | Davies | ............... | A61M 15/08 222/162 |
| 2007/0056585 A1 * | 3/2007 | Davies | .............. | A61M 15/0065 128/203.15 |

\* cited by examiner

WASHING WATER SPRAYING VESSEL FOR NASAL CAVITY CLEANER

CROSS-REFERENCE TO RELATED APPLICATIONS

This U.S. non-provisional patent application claims the benefit of priority under 35 U.S.C. §119 of Korean Patent Application No. 10-2012-0041652, filed Apr. 20, 2012, and Korean Patent Application No. 10-2013-0011625, filed Feb. 1, 2013, the entire contents of which are hereby incorporated by reference for all purposes.

BACKGROUND OF THE INVENTION

The present invention disclosed herein relates to a washing water spraying vessel for a nasal cavity cleaner, and more particularly, to a washing water spraying vessel for a nasal cavity cleaner for performing a pumping operation of a pumping member only when a pair of buttons formed on both sides of an outer cap are simultaneously pressed, which allows enabling fundamentally blocking the pumping operation through external pressure unintended by a user, thereby not only preventing washing water from being unnecessarily consumed but also preventing an inner part of an overcap from being contaminated.

Generally, washing water spraying vessels for a nasal cavity cleaners are containers for curing all kinds of the diseases in a nasal cavity or eliminating impurities, and preventing dryness by inserting washing water into the nasal cavity, and it is said that the nasal cavity comprises the front unit connected to the outside through nares, and the rear unit connected to a pharynx through a choana.

The washing water inserted into the above-mentioned washing water spraying vessel for a nasal cavity cleaner generally uses a saline solution of 3%, and, recently, functional washing water containing various ingredients as well as bamboo salt is being improved.

Recently, a harmful substance is accumulated, or various respiratory diseases, a pollen allergy and the flu often appear, by inhaling, through a mouth and a nose, air pollution caused by car exhaust fumes, pollen and a yellow dust in springtime, a cold virus going during the change of seasons, and the like. Therefore, the number of people exhibiting snoring symptoms is being increased.

It is already proved through many medical reports that washing the nasal cavity is effective in all kinds of the respiratory diseases, and patients who suffer from all kinds of the respiratory diseases wash the nasal cavity several times a day.

With reference to Utility Model Registration No. 20-0165667, a conventional washing water spraying vessel for a nasal cavity cleaner is described below. Referring to the registered utility model, the conventional washing water spraying vessel for a nasal cavity cleaner comprises a container 100 receiving a cleaning liquid, a lid 200 screw-coupled in a spout portion of the container 100, a nozzle 300 vertically movably coupled to the lid 200, in which a hanging part 310 for allowing vertically moving a finger to hang is formed in a lower part, a bottom liquid chamber 320 is formed in an inner top, and a spurting opening 321 for spurting the cleaning liquid in an upper part, an adjustment rod 330 inserted into the bottom liquid chamber 320 of the nozzle 300, for uniformly and thinly spraying the cleaning liquid, and valves 550, 551 for spurting through the spurting opening 321 the cleansing liquid after the cleansing liquid included in the container 100 is stored in the bottom liquid chamber 310 by vertically moving the nozzle 300.

In the washing water spraying vessel for a nasal cavity cleaner consisting of the above-described configuration, it is configured that the nozzle 300 is coupled to the lid 200 of the container 100 to be upwardly slid, so that the cleansing liquid is spurted by the operation of the valves 550, 551 of an inner side according to repeatedly perform pressing by putting the finger in the hanging part 310. Therefore, it is easy to portably use it.

However, the washing water spraying vessel for a nasal cavity cleaner has a structure of spurting the cleansing liquid upon pressing the upper part of the hanging part 310. Therefore, when the user keeps the washing water spraying vessel for a nasal cavity cleaner in a bag portably, even if the user does not operate, the cleansing liquid is spilled by pressing the hanging part 310, and thus, the contents may be unnecessarily consumed, and the inside of the overcap may be contaminated.

SUMMARY OF THE INVENTION

The present invention has been made in order to solve the above-described problem. The present invention provides a washing water spraying vessel for a nasal cavity cleaner for performing a pumping operation of a pumping member only when a pair of buttons formed on both sides of an outer cap are simultaneously pressed, which enables fundamentally blocking the pumping operation through external pressurizing unintentionally by the user, thereby not only preventing washing water from unnecessarily being consumed but also preventing the inner part of the overcap from being contaminated.

In addition, the present invention provides a washing water spraying vessel for a nasal cavity cleaner in which by rotating both the overcap and a nozzle to be interlocked, the descent of the nozzle is not performed by discrepantly locating a guide groove of the nozzle with an up-and-down guide protrusion on a state that the overcap cannot be detached by rotating the overcap to one direction, and the descent of the nozzle is performed by locating a guide groove of the nozzle in the upright direction on an up-and-down guide protrusion on a state that the overcap can be detached by rotating the overcap to the other direction. This makes it possible to fundamentally block the pumping operation through external pressure unintended by the user, thereby not only preventing washing water from being unnecessarily consumed, but also preventing the overcap from being lost.

In order to solve the above-described problem, the washing water spraying vessel for a nasal cavity cleaner according to the present invention comprises a container body receiving the contents; an inner cap having a cylindrical shape while covering an upper part of the container body, with an elastic body installed in the inner side; a nozzle ascending and descending in an upper part of the inner cap while being supported by the elastic body; a couple of outer caps covering the inner cap, which comprises a pair of buttons giving pressure to the nozzle, moving inwards by pressurizing by a user on both sides of the upper part to press the nozzle; a pumping member for discharging the contents outwardly through a pumping operation by an up-and-down movement of the nozzle; a coupling part coupled to the upper portion of the outer cap, thereby fixing an overcap; an overcap detachable coupled to the coupling part while covering the nozzle.

Further, on both sides of an outer circumference surface of the inner cap, it is featured that an up-and-down guide protrusion guiding an ascent and a descent of the outer cap is built protrudingly In addition, the nozzle comprises a guide groove which is supported by the elastic body and move along the up-and-down guide protrusion on the lower end of the nozzle, a body which forms a pair of pumping guide protrusions having a slope surface in both side directions, which gets narrower as the surface goes up from the lower part to the upper part, and a coupling pipe which presses the pumping member by being protrusion-formed upwardly between the pair of pumping guide protrusions and being coupled to the pumping member.

In addition, on an inner side of the button, a pressing protrusion for pressing the pumping guide protrusion is formed.

In addition, on the outer circumference surface of the inner cap, a rotation preventing protrusion is formed to prevent rotation of the outer cap, and on an inner circumference surface of the outer cap, a rotation preventing groove coupled to the rotation preventing protrusion is formed.

In addition, on the outer circumference surface of the inner cap, a separation preventing protrusion is formed to prevent the outer cap from separating upwardly, and on the inner circumference surface of the outer cap, a hanging protrusion coupled to the separation preventing protrusion is formed.

Moreover, on both sides of an outer circumference surface of the nozzle, a section is formed to interlock with the overcap and rotate together according to rotation of the overcap, and the inner circumference surface of the overcap is configured as a shape corresponding to the section.

Furthermore, on a lower portion of the nozzle, a seating groove seated on an upper part of the up-and-down guide protrusion, and the lengths of lower end portions of the seating groove are formed to have different ends so as to climb over the up-and-down guide protrusion upon rotation of the nozzle.

In addition, on both sides of a lower portion of the coupling part in contact with the button, a cutting groove is formed to prevent interference upon moving the button inwards.

In addition, on an outer circumference surface of an upper portion of the coupling part, a pair of corresponding rotation limitation grooves is formed to limit a rotation range of the overcap, and on the inner circumference surface of the overcap, a rotation limitation protrusion which moves in the rotation limitation groove is formed.

Further, on the rotation limitation groove, an upper end of a leading edge is partially opened to enable insertion or withdrawal of the rotation limitation protrusion.

Furthermore, on a terminal portion of the rotation limitation groove, a support groove which supports the rotation limitation groove in a close state after the overcap rotates to one direction is formed.

As described above, according to the present invention, the pumping operation of the pumping member is performed only when the pair of buttons formed on both sides of the outer cap are simultaneously pressed, which allows enabling fundamentally blocking the pumping operation through unintended external pressure by a user, thereby not only preventing the washing water from unnecessarily being consumed but also preventing the inner part of the overcap from being contaminated.

Furthermore, according to the present invention, by rotating both the overcap and a nozzle to be interlocked, the descent of the nozzle is not performed by discrepantly locating a guide groove of the nozzle with an up-and-down guide protrusion on a state that the overcap cannot be detached by rotating the overcap to one side, and the descent of the nozzle is performed by locating a guide groove of the nozzle in the upright direction on an up-and-down guide protrusion on a state that the overcap can be detached by rotating the overcap to the other side. This makes it possible to fundamentally block the pumping operation through external pressure unintended by the user, thereby not only preventing washing water from being unnecessarily consumed, but also preventing the overcap from being lost.

In addition, the pumping operation is performed through pressurizing sides of the buttons, which is able to make a vertical movement of the container stop upon the pumping movement. Therefore, this makes it possible to fundamentally prevent the inside of a nose from being damaged due to impact of a coupling pipe inserted into the nose upon the operation of pumping.

DETAILED DESCRIPTION OF PREFERRED EMBODIMENTS

Hereinafter, exemplary embodiments of the present invention will be described in detail with reference to the accompanying drawings. The same reference numerals provided in the drawings indicate the same members.

Figure 1:
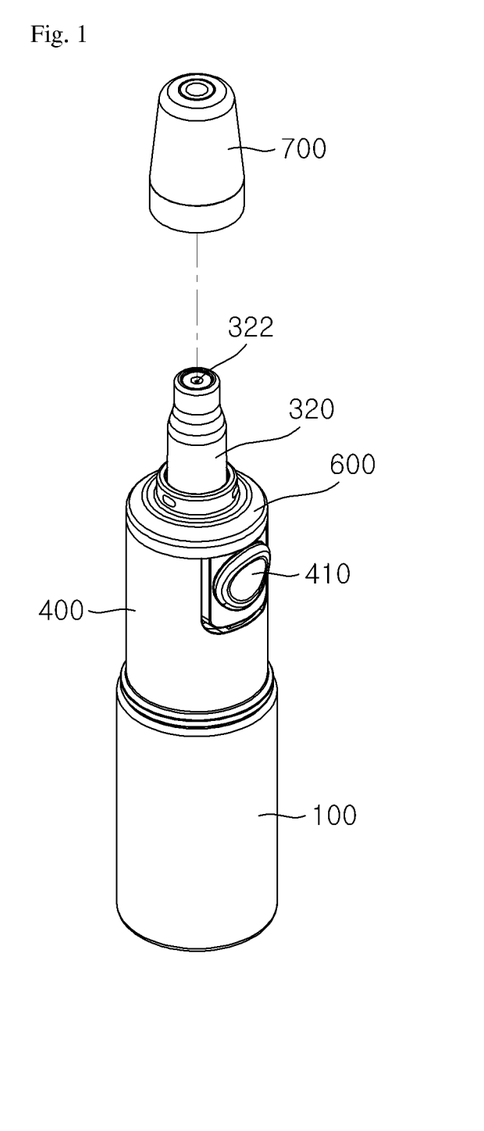
FIG. 1 is a coupling perspective view illustrating a configuration of a washing water spraying vessel for a nasal cavity cleaner according to an exemplary embodiment of the present invention.
Figure 2:
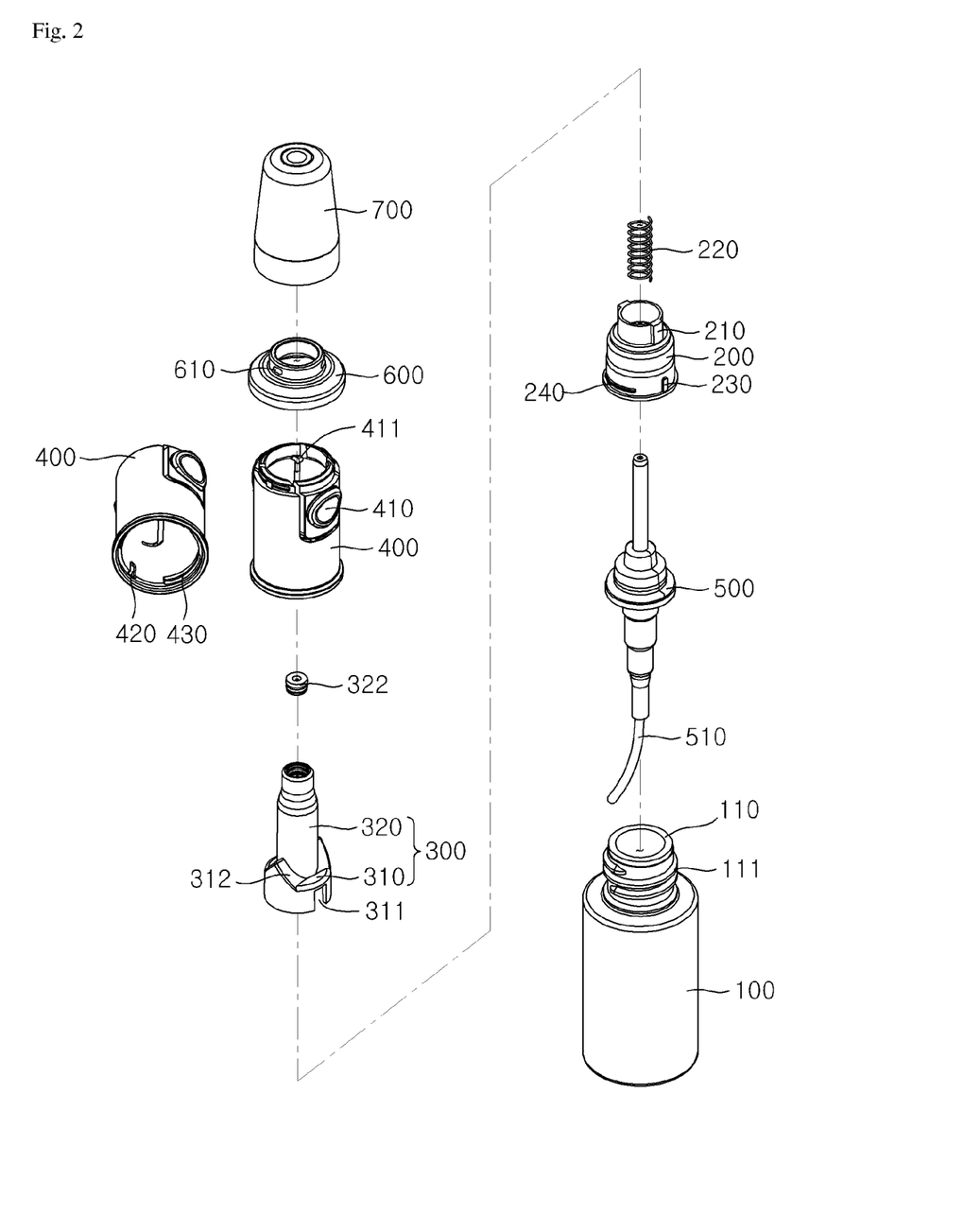
FIG. 2 is an exploded perspective view illustrating a configuration of a washing water spraying vessel for a nasal cavity cleaner according to an exemplary embodiment of the present invention.
Figure 3:
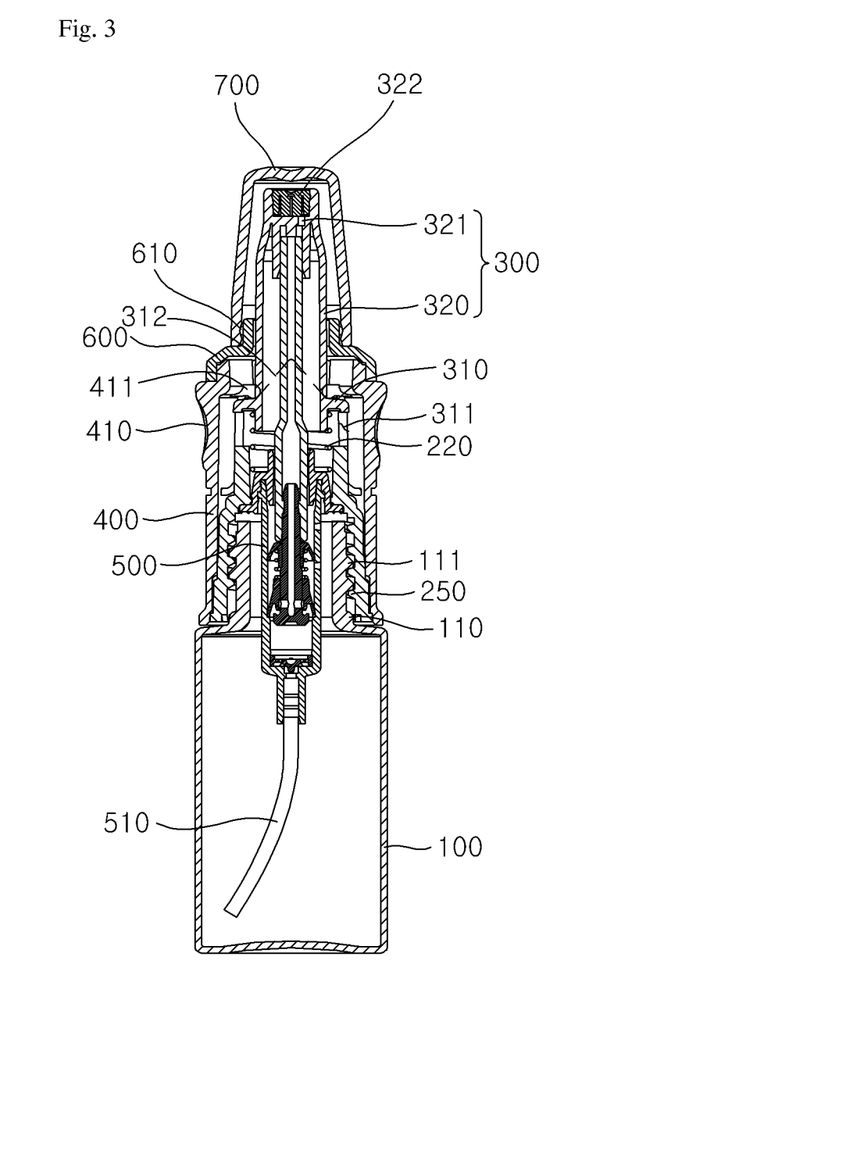
FIG. 3 is a cross-sectional view illustrating a configuration of a washing water spraying vessel for a nasal cavity cleaner according to an exemplary embodiment of the present invention.

FIG. 1 is a coupling perspective view illustrating a configuration of a washing water spraying vessel for a nasal cavity cleaner according to an exemplary embodiment of the present invention, FIG. 2 is an exploded perspective view illustrating a configuration of a washing water spraying vessel for a nasal cavity cleaner according to an exemplary embodiment of the present invention, and FIG. 3 is a cross-sectional view illustrating a configuration of a washing water spraying vessel for a nasal cavity cleaner according to an exemplary embodiment of the present invention.

Referring to FIGS. 1 to 3, a washing water spraying vessel for a nasal cavity cleaner according to an exemplary embodiment of the present invention comprises a container body 100, an inner cap 200, a nozzle 300, an outer cap 400, a pumping member 500, a coupling member 600 and an overcap 700.

In the container body 100, the contents are received, and a discharging part 110 which allows discharging the contents is formed on an upper portion of the container body 100. On an outer circumference surface of the discharging part 110, a first screw thread 111 is formed to be screw-coupled to the inner cap 200 which will be described later.

The inner cap 200 may have a cylindrical shape coupled to the discharging part 110 while covering the upper portion of the container body 100, and on an inner circumference surface, a second screw thread 250 is formed to be screw-coupled to the first screw thread 111.

In accordance with the present invention, in the inner surface of the inner cap 200, an elastic body 220 supporting a lower end of the nozzle 300, which will be described later, is formed, and the elastic body 220 supplies an elastic force to the nozzle 300 descending by pressure of the button 410, so that, when the pressure of the button 410 is removed, the nozzle 300 is allowed to move upwardly, thereby restoring the button 410 in the state of to being pressed.

In addition, on both sides of the outer circumference surface of the upper portion of the inner cap 200, an up-and-down guide protrusion 210 which guides the ascent/descent of the nozzle 300 to be described later is protruded, and the up-and-down guide protrusion 210 is inserted to a guide groove 311 of the nozzle 200 upon ascending or descending of the nozzle 300, so that the nozzle 300 is guided to ascend or descend vertically without twisting horizontally.

Meanwhile, on an outer circumference surface of a lower portion of the inner cap 200, a rotation preventing protrusion 230 is formed to prevent the rotation of the outer cap 400, and a separation preventing protrusion 240 is formed to prevent the outer cap 400 from being separated upwardly.

The nozzle 300 ascends or descends on the upper portion of the inner cap 200 while being supported by the elastic body 220, further comprising a body 310 and a coupling 320.

The body 310 is supported by the elastic body 220, and is coupled to the upper portion of the inner cap 200 while covering the upper portion of the inner cap 200. On a lower end thereof, a guide groove 311 which moves along the up-and-down guide protrusion 210 upon ascending or descending the nozzle 300 by cutting part of a portion in contact with the up-and-down guide protrusion 210 is formed.

Meanwhile, according to the present invention, in an upper end of the body 310 is formed a pair of pumping guide protrusions 312 having a slope in both directions so that a width gets narrower from the lower part toward the upper part, and the pumping guide protrusion 312 guides the nozzle 300 to descend by pressure of a pressure protrusion 411 according to manipulation of a button 410 of the outer cap which will be described later.

The coupling pipe 320 is protruded between the pair of pumping guide protrusions 312, that is, from a center of an upper end of the body 310 to an upward direction, and in the inner side thereof, an upper portion of a pumping member 500 is coupled. This makes it possible to perform a pumping operation of the pumping member 500 by transferring pressure to the pumping member 500 when the nozzle 300 descends in accordance with pressurization by a user.

On an upper end of the coupling pipe 320, a discharging hole 321 for discharging the contents moved by the pumping operation of the pumping member 500, and a nozzle tip 322 for discharging the contents to the outside is coupled to an upper portion of the discharging hole 321.

The outer cap 400 having a cylindrical shape is coupled, covering the inner cap 200. Both sides of the upper portion of the outer cap 400 comprise a button 410 for pressing the nozzle 300 while moving inwardly by the user pressure. In the inside of the button 410, the pressing protrusion 411 for pressing the pumping guide protrusion 312 is formed, and when the button 410 moves to the inside, the pressing protrusion 411 presses the pumping guide protrusion 312, so that the pumping operation can be performed according to the descent of the nozzle 300

Meanwhile, on the inner circumference surface of the outer cap 400, a rotation preventing groove 420 which is coupled to the rotation preventing protrusion 230 to prevent a rotation of the outer cap 400, is formed, and a hanging protrusion 430 is coupled to the separation preventing protrusion 240 to prevent the outer cap 400 from being separated from the inner cap 300.

The pumping member 500 is coupled to the inner side of the nozzle 300, and discharges the contents outwardly by the pumping operation caused by the ascent/descent movement of the nozzle 300. A suction pipe 510 for suctioning the contents received in the container body 100 is coupled to a lower end of the pumping member 500. Each function and construction of the pumping member 400 is a prior art of technological field where the present invention belongs to; therefore detailed description will be omitted.

The coupling part 600 is coupled to the upper portion of the outer cap 400 in order to fix the overcap 700. On its outer circumference surface, a coupling protrusion 610 is preferably formed to allow the overcap 700 to be coupled.

The overcap 700 covers the coupling pipe 320 of the nozzle 300, and is coupled to the coupling part 600 coupled to the upper portion of the outer cap 400, further coupled to the coupling protrusion 610 formed on the coupling part 600 and protecting the nozzle tip 322 from external impact.

Figure 4:
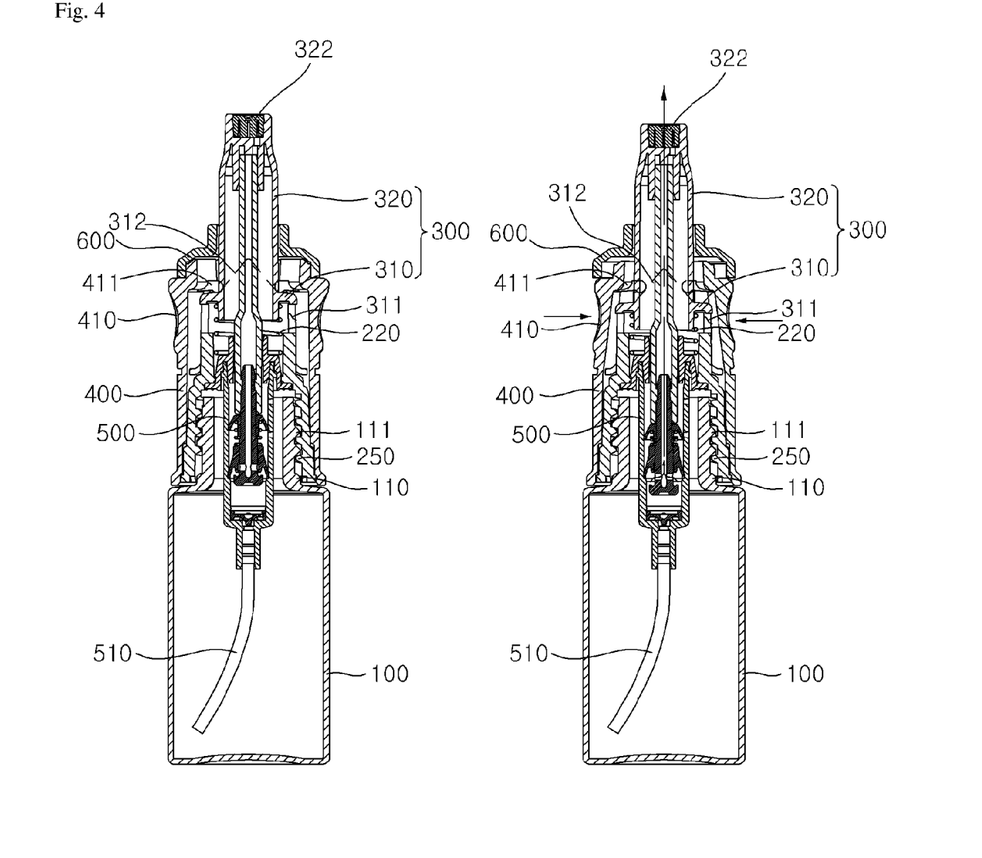
FIG. 4 is a view illustrating an operation state of a washing water spraying vessel for a nasal cavity cleaner according to an exemplary embodiment of the present invention.

Hereinafter, with reference to FIG. 4, a method of using a washing water spraying vessel for a nasal cavity cleaner according to an exemplary embodiment of the present invention is described. FIG. 4 is a view illustrating an operation state of a washing water spraying vessel for a nasal cavity cleaner according to an exemplary embodiment of the present invention.

Referring to FIG. 4, in a washing water spraying vessel for a nasal cavity cleaner according to an exemplary embodiment of the present invention, when a pair of buttons 410 installed in both sides of the upper portion of the outer cap 400 are simultaneously pressed, the buttons 410 move inwardly, when the pressing protrusion 411 formed on an inner side of the button 410 presses the pumping guide protrusion 312 of the nozzle 300.

As described above, if the pressing protrusion 411 presses the pumping guide protrusion 312, the nozzle 300 descends by the slope of the pumping guide protrusion 312, and as the nozzle 300 descends, the pumping member 500 coupled to the inner side of the nozzle 300 descends together, generating a pumping operation and thereby discharging the contents received in the container body 100.

Hereinafter, with reference to FIGS. 5 to 11, a washing water spraying vessel for a nasal cavity cleaner according to another embodiment of the present invention will be described.

Figure 5:
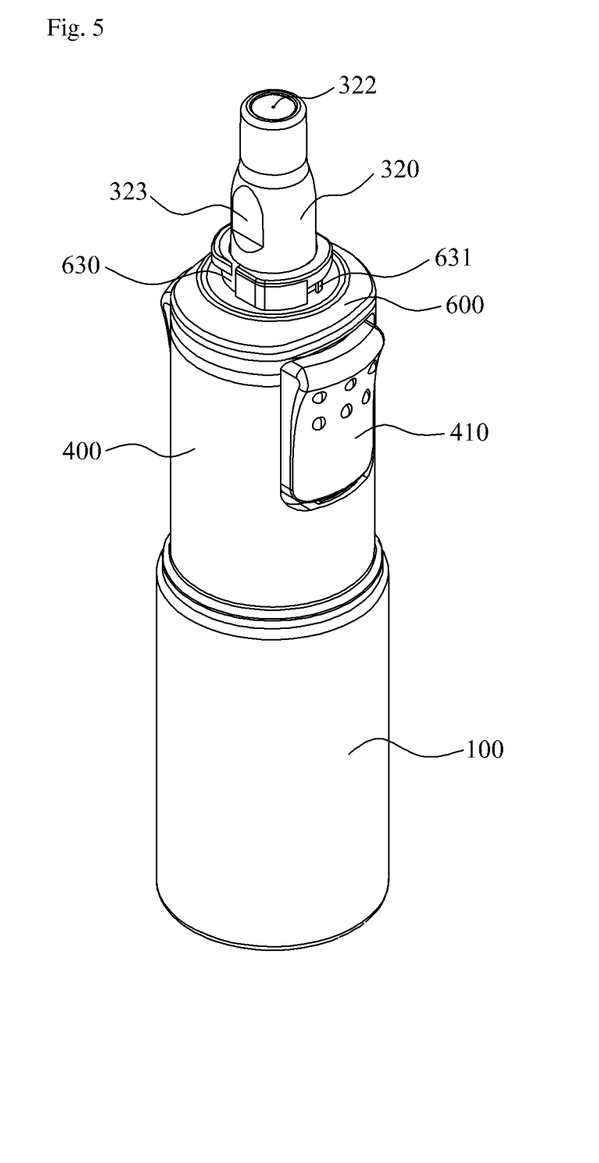
FIG. 5 is a coupling perspective view illustrating a configuration of a washing water spraying vessel for a nasal cavity cleaner according to another embodiment of the present invention.
Figure 6:
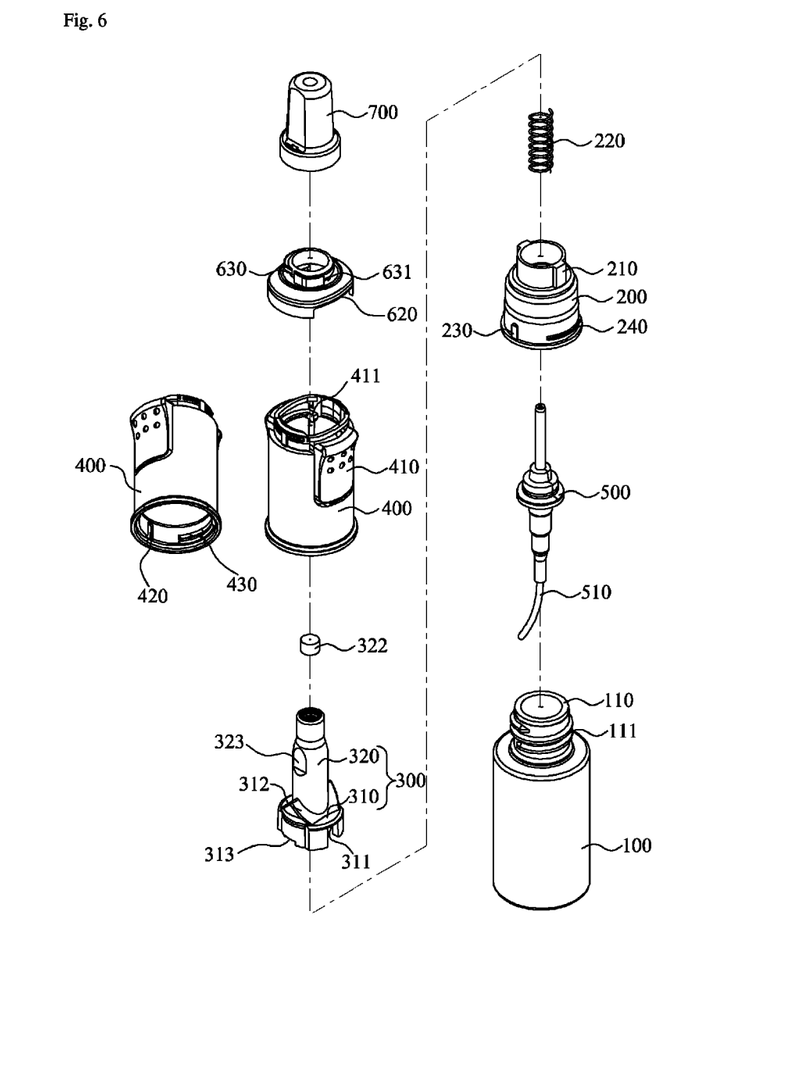
FIG. 6 is an exploded perspective view illustrating a configuration of a washing water spraying vessel for a nasal cavity cleaner according to another embodiment of the present invention.
Figure 7:
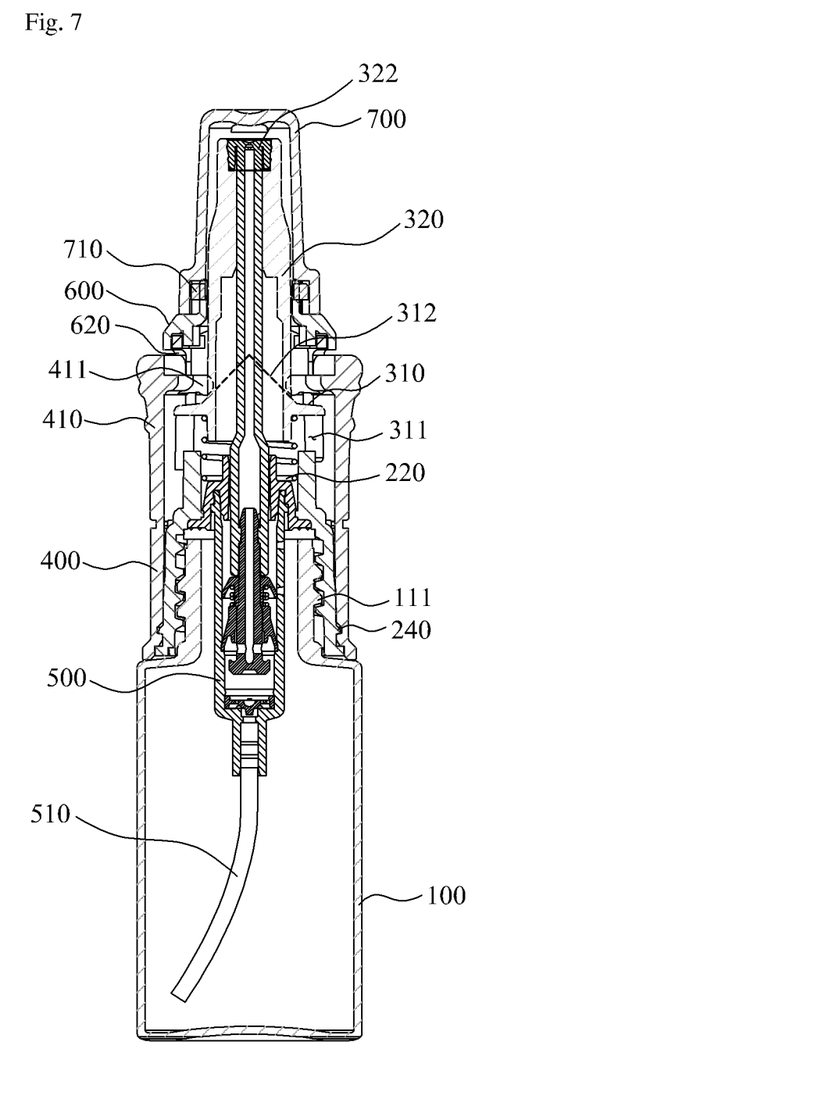
FIG. 7 is a cross-sectional view illustrating a configuration of a washing water spraying vessel for a nasal cavity cleaner according to another embodiment of the present invention.

FIG. 5 is a coupling perspective view illustrating a configuration of a washing water spraying vessel for a nasal cavity cleaner according to another embodiment of the present invention, FIG. 6 is an exploded perspective view illustrating a configuration of a washing water spraying vessel for a nasal cavity cleaner according to another embodiment of the present invention, and FIG. 7 is a cross-sectional view illustrating a configuration of a washing water spraying vessel for a nasal cavity cleaner according to another embodiment of the present invention.

Figure 8:
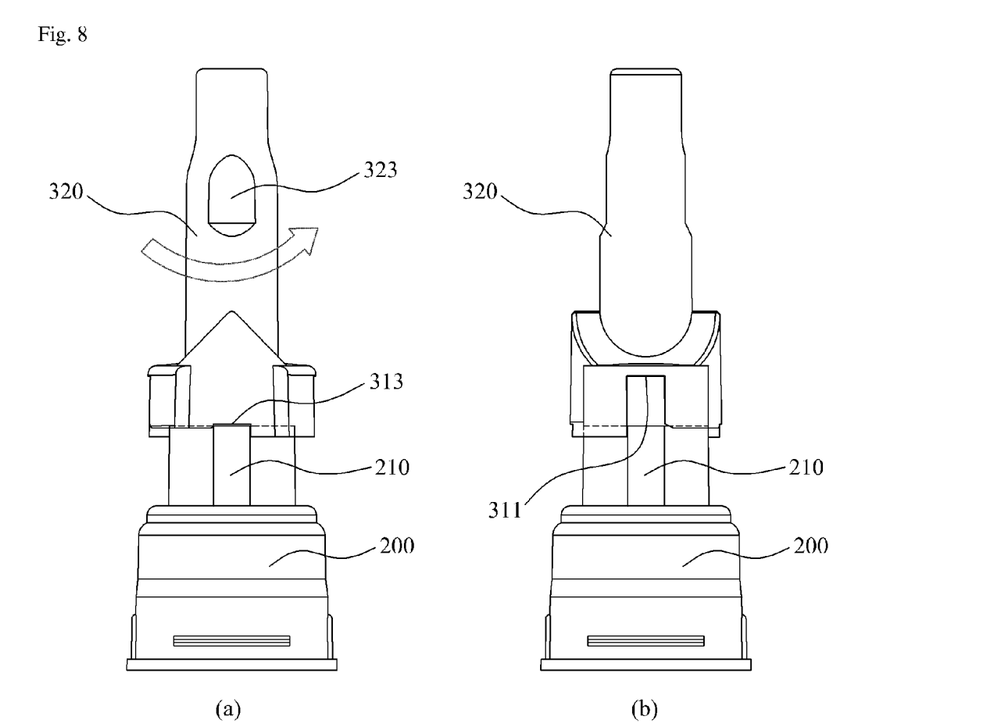
FIG. 8 is a view illustrating a configuration a rotation state of a washing water spraying vessel for a nasal cavity cleaner according to another embodiment of the present invention.
Figure 9:
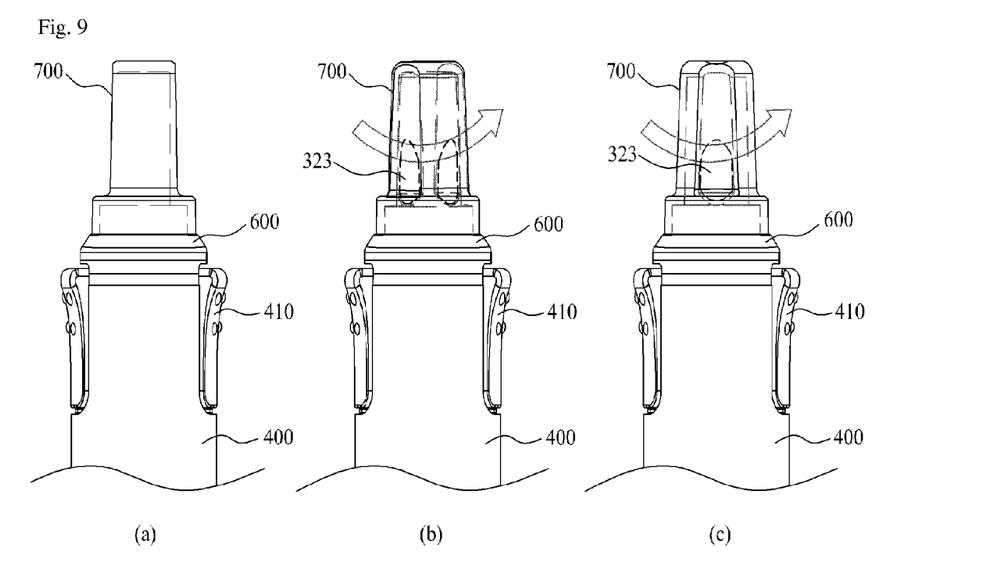
FIGS. 9 and 10 are views illustrating a process of detaching an overcap according to a rotation of the overcap and a nozzle of a washing water spraying vessel for a nasal cavity cleaner according to another embodiment of the present invention.
Figure 10:
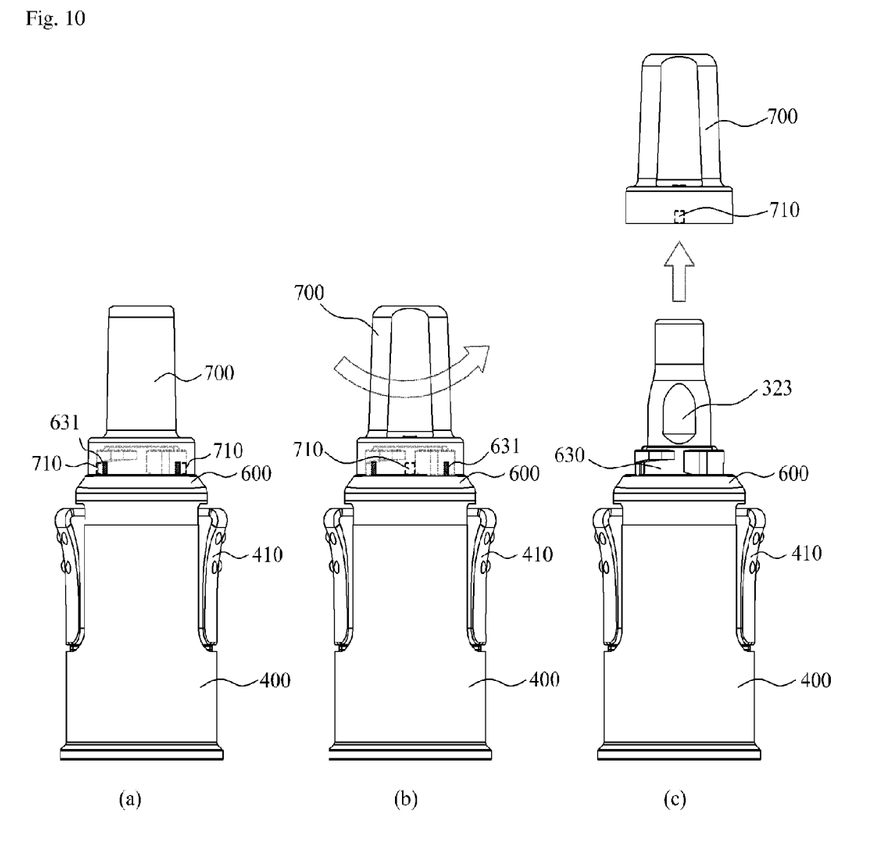
Figure 11:
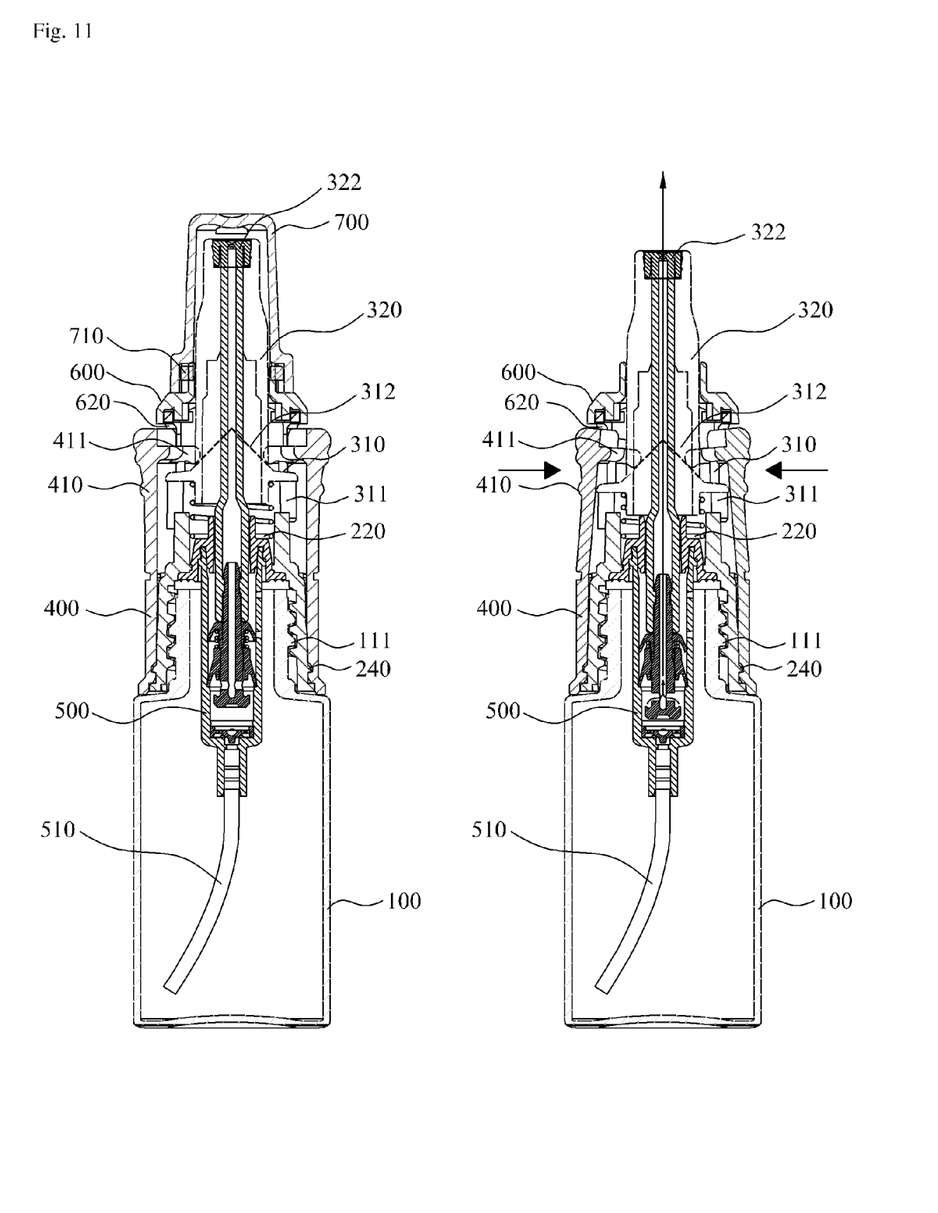
FIG. 11 is a view illustrating an operation state of a washing water spraying vessel for a nasal cavity cleaner according to another embodiment of the present invention.

FIG. 8 is a view illustrating a configuration a rotation state of a washing water spraying vessel for a nasal cavity cleaner according to another embodiment of the present invention, FIGS. 9 and 10 are views illustrating a process of detaching an overcap according to a rotation of the overcap and a nozzle of a washing water spraying vessel for a nasal cavity cleaner according to another embodiment of the present invention, and FIG. 11 is a view illustrating an operation state of a washing water spraying vessel for a nasal cavity cleaner according to another embodiment of the present invention.

With reference to FIGS. 5 to 11, a washing water spraying vessel for a nasal cavity cleaner according to another embodiment of the present invention includes a container body 100, an inner cap 200, a nozzle 300, an outer cap 400, a pumping member 500, a coupling part 600, and an overcap 700.

The container body 100, the inner cap 200, the outer cap 400, and the pumping member 500 are the same as described in an exemplary embodiment of the present invention. Hereinafter, only the nozzle 300, the coupling part 600, and the overcap 700 are described.

The nozzle 300 ascends to the upper portion of the inner cap 200 and guides a pumping operation of the pumping member 500 while being supported by the elastic body 220, and the nozzle 300 of another embodiment of the present invention is configured to rotate together with the overcap 700.

The nozzle 300 comprises a section 323 on both sides of the outer circumference surface, and the section 323 is configured to be in contact with an inner circumference surface of the overcap 700, so that the nozzle 300 can rotate together according to a rotation of the overcap 700.

Furthermore, according to the present invention, by rotating both the overcap and a nozzle to be interlocked, the descent of the nozzle is not performed by discrepantly locating a guide groove of the nozzle with an up-and-down guide protrusion on a state that the overcap cannot be detached by rotating the overcap to one side, and the descent of the nozzle is performed by locating a guide groove of the nozzle in the upright direction on an up-and-down guide protrusion on a state that the overcap can be detached by rotating the overcap to the other side. On the lower end of the nozzle 300, a seating groove 313 seated in an upper end of the up-and-down guide groove 210 is formed in the closed state wherein the overcap 700 rotates 90 degrees and therefore cannot be detached.

On the upper end of the up-and-down guide groove 210 is seated the seating groove 313, which allows stopping descending the nozzle 300.

In accordance with the present invention, as illustrated in FIG. 8, one side of the seating groove 313 has a shorter length than the other, and so as to climb over the up-and-down guide protrusion 210 upon the rotation of the nozzle 300, the lengths of lower end portions of the seating groove 313 should be different from each other; the part which climbs over the up-and-down guide protrusion 210 is preferably shorter and has a round end in order not to generate interference upon the rotation of the nozzle 300.

Meanwhile, the guide groove 311, when the overcap 700 in the close state rotate in a reverse direction 90 degrees and then becomes to the opposite direction, gets to be located right over the up-and-down guide protrusion 210, and thereby can be ascended or descended by pressure of the button 410.

Similarly, one side of the guide groove 311 has a shorter length than the other, and so as to climb over the up-and-down guide protrusion 210 upon the rotation of the nozzle 300, the lengths of lower end portions should be different from each other; The parts which climbs over the up-and-down guide protrusion 210 are preferably shorter and has a round end in order not to generate interference upon the rotation of the nozzle 300.

The coupling part 600 is coupled to the upper portion of the outer cap 400 and fixes the overcap 700, comprising a cutting groove 620, wherein the button 410 can move on both sides of the lower portion where it is in contact with the button 410, in order to prevent interference when the coupling part 600 moves into inner direction of the button 410 according to pressure of the button 410.

Meanwhile, according to the present invention, on the outer circumference surface of the coupling part 600, a pair of corresponding rotation limiting grooves 630 is formed to limit a rotation range of the overcap 700. The rotation limiting protrusion 710 formed on the overcap 700 is inserted and moves within the rotation limiting groove 630 according to the rotation of the overcap 700, whereas an upper end of a leading edge of the rotation limiting groove 630 is partially opened so that the rotation limiting groove 630 of the rotation limiting protrusion 710 can be inserted or withdrawn.

In addition, the bottom of the rotation limiting groove 630 preferably has an oval shape, in order to prevent the rotation limiting groove 630 from rotating together when the overcap 700 is rotating. At this time, a support protrusion 631 for supporting the rotation limiting protrusion 710 of the overcap 700 in the close state by rotating the overcap 700 to one side is formed.

Meanwhile, an upper portion of the coupling part 600 is ovally configured to prevent rotating together upon the rotation of the overcap 700, and at this time, the upper portion of the outer cap 400 that is coupled to the lower portion of the coupling part 600 is preferably made oval.

The overcap 700 is coupled to the coupling 600 while covering the coupling pipe 320 of the nozzle 300, allowing it to be detached, and the overcap 700 of another embodiment of the present invention is configured to be rotatable to one direction or the other.

The inner circumference surface of the overcap 700 has a shape corresponding to the section 323 of the nozzle 300 so that the overcap 700 rotates together with the nozzle 300 by interlocking with the nozzle 300 upon rotating. When the nozzle rotates together, a location of the guide groove 311 of the nozzle 300 is changed depending on the rotation of the overcap 700, from which it is possible to control an ascent or a descent of the nozzle 300 according to the location of the guide groove 311.

In the condition when the overcap 700 rotates in one direction and is not detachable, the guide groove 311 of the nozzle 300 should be dislocated with the up-and-down guide protrusion 210 so that the nozzle 300 does not descend; in the condition when the overcap 700 rotates in the other direction and is detached, the guide groove 311 of the nozzle 300 is located right above the up-and-down guide protrusion 210, so that the nozzle 300 can descend; therefore, in the condition when the overcap 700 combines with the coupling part 600, the nozzle 300 does no descend, so that it is possible to fundamentally block a pumping operation of the pumping member 500, thereby preventing washing water from being unnecessarily consumed by unintentional external pressure by a user.

Meanwhile, on the inner circumference surface of the overcap 700, the rotation limiting protrusion 710 moving in the rotation limiting groove 630 is formed. As illustrated in FIG. 10, the rotation limiting protrusion 710 is inserted to an open position in an upper end of a leading edge of the rotation limiting groove 630, and moves in the rotation limiting groove 630 depending on the rotation of the overcap 700. In a close state when the overcap 700 rotates to one direction and cannot be detached, the rotation limiting protrusion 710 is configured to be supported by the support protrusion 631 of the coupling part 600, and in an open state when the overcap 700 rotates to the other direction, and can be detached, the overcap 700 is configured to be placed on an open location on the upper end of the leading edge of the rotation limiting groove 630.

Hereinafter, referring to FIGS. 9 to 11, a method of using a washing water spraying vessel for a nasal cavity cleaner according to another embodiment of the present invention is described. FIGS. 9 and 10 are views illustrating a process of detaching an overcap according to a rotation of the overcap and a nozzle of a washing water spraying vessel for a nasal cavity cleaner according to another embodiment of the present invention, and FIG. 11 is a view illustrating an operation state of a washing water spraying vessel for a nasal cavity cleaner according to another embodiment of the present invention.

With reference to FIGS. 9 to 11, in a washing water spraying vessel for a nasal cavity cleaner according to another embodiment of the present invention, initially when the overcap 700 is grasped and rotates 90 degrees to the other direction in the state when the overcap 700 rotates to one direction, and cannot be detached, the rotation limiting protrusion 710 of the overcap 700 moves to the open location in the upper end of the leading edge of the rotation limiting groove 630, and at this time, the nozzle 300 interlocking the overcap 700 rotates together, and the guide groove 300 of the nozzle 300 is placed right over the up-and-down guide protrusion 210.

Next, when the overcap 700 rotates to the other direction and is moved upwards, the rotation limiting protrusion 710 is withdrawn according to the open location of the leading edge of the rotation limiting groove 630, so that the overcap 700 is detached from the coupling 600.

As described above, if a pair of buttons included in both sides of the upper portion of the outer cap 400 are pressed simultaneously after detaching the overcap 700, the button 410 moves inwards, and at this time, the pressing protrusion 411 formed in the inner surface of the button 410 presses the pumping guide protrusion 312 of the nozzle 300.

As described above, if the pressure protrusion 411 presses the pumping guide protrusion 312, the nozzle 300 descends by the slope of the pumping guide protrusion 312, and according to the descending of the nozzle 300, the pumping member 500 descends together combined to the inside of the nozzle 300, thereby generating the pumping operation and discharging the contents contained in the container body 100.

As stated above, in a washing water spraying vessel for a nasal cavity cleaner according to another embodiment of the present invention, the ascent or the descent of the nozzle 300 according to the rotation of the overcap 700 is configured to be controlled, which allows the pumping operation of the pumping member 500 to be stopped in the state when the overcap 700 is closed, and prevents the contents from being unnecessarily consumed by unintentional external pressure by a user.

The best embodiments of the present invention are described with reference to the drawings and the specification. Here, even though particular terms are used, they are used to explain the present invention, not to limit their meanings or the range of the present invention described in the claims. Therefore, it will be understood by those skilled in the art that various changes in form and other equivalent embodiments may be made therefrom. Accordingly, the truly technical protection scope of the present invention is to be determined by the technical spirit of the appended claims.

What is claimed is:

1. A washing water spraying vessel for a nasal cavity cleaner, comprising:
   a container body for receiving contents;
   an inner cap having a cylindrical shape and coupled to the container body while covering an upper portion of the container body, wherein an elastic body is equipped at an inner side of the inner cap;
   a nozzle capable of ascending or descending in an upper portion of the inner cap while being supported by the elastic body;
   an outer cap coupled to the inner cap while covering the inner cap, comprising a pair of buttons for moving inwards by a user pressure at both sides of an upper portion of the outer cap to press the nozzle;
   a pumping member for discharging the contents outwards through a pumping operation by the ascending or descending of the nozzle;
   a coupling part coupled to an upper portion of the outer cap to fix an overcap; and
   the overcap detachably coupled to the coupling part while covering the nozzle, wherein the overcap is removed so the nozzle can be inserted to dispense the contents,
   wherein a section is formed on both sides of an outer circumference surface of the nozzle to rotate together according to a rotation of the overcap by interlocking with the overcap, and an inner circumference surface of the overcap has a shape corresponding to the section.

2. The washing water spraying vessel for a nasal cavity cleaner of claim 1, wherein on both sides of an outer circumference surface of the upper portion of the inner cap, an up-and-down guide protrusion for guiding ascending or descending the outer cap is formed.

3. The washing water spraying vessel for a nasal cavity cleaner of claim 2, wherein the nozzle is supported by the elastic body, and on a lower end of the nozzle, a guide groove is formed to move along the up-and-down guide protrusion, and on an upper end of the nozzle, a body forms a pair of pumping guide protrusions having a slope in both directions so that a width gets narrower from the lower portion toward the upper portion, and a coupling pipe is protruded upwardly between the pair of pumping guide protrusions and coupled to the pumping member, thereby pressurizing the pumping member.

4. The washing water spraying vessel for a nasal cavity cleaner of claim 3, wherein a pressing protrusion for pressing the pumping guide protrusion is formed on an inner side of the button.

5. The washing water spraying vessel for a nasal cavity cleaner of claim 1, wherein a rotation preventing protrusion is formed on an outer circumference surface of the inner cap to prevent the outer cap from rotating, and wherein a rotation preventing groove coupled to the rotation preventing protrusion is formed on an inner circumference surface of the outer cap.

6. The washing water spraying vessel for a nasal cavity cleaner of claim 1, wherein a separation preventing protrusion is formed on the outer circumference surface of the inner cap to prevent the outer cap from separating upwardly, and a hanging protrusion coupled to the separation preventing protrusion is formed on the inner circumference surface of the outer cap.

7. The washing water spraying vessel for a nasal cavity cleaner of claim 1, wherein a seating groove seated in an upper end of the up-and-down protrusion is formed on a lower end of the nozzle, wherein lengths of lower end portions of the seating groove are formed to have an end difference so that they can be different from each other, so as to climb over the up-and-down guide protrusion upon a rotation of the nozzle.

8. The washing water spraying vessel for a nasal cavity cleaner of claim 1, wherein on both sides of a lower portion of the coupling part in contact with the button, a cutting groove is formed to prevent interference upon moving the button inwards.

9. The washing water spraying vessel for a nasal cavity cleaner of claim 1, wherein on an outer circumference surface of an upper portion of the coupling part, a pair of corresponding rotation limitation grooves is formed to limit a rotation range of the overcap, and on the inner circumference surface of the overcap, a rotation limitation protrusion which moves within the rotation limitation groove is formed.

10. The washing water spraying vessel for a nasal cavity cleaner of claim 9, wherein an upper end of a leading edge of the rotation limiting groove is partially opened so that the rotation limiting protrusion can be inserted or withdrawn.

11. The washing water spraying vessel for a nasal cavity cleaner of claim 9, wherein in a bottom of the rotation limiting groove, a support protrusion for supporting the rotation limiting protrusion of the overcap in a close state by rotating the overcap to one side is formed.

* * * * *